(12) United States Patent
Schachar et al.

(10) Patent No.: US 10,849,855 B2
(45) Date of Patent: Dec. 1, 2020

(54) METHODS AND DEVICES FOR TREATING A RETINAL DETACHMENT

(71) Applicant: VITREAN, INC., Palo Alto, CA (US)

(72) Inventors: Ira Hyman Schachar, Palo Alto, CA (US); Ronald A. Schachar, La Jolla, CA (US)

(73) Assignee: VITREAN, INC., Palo Alto, CA (US)

(*) Notice: Subject to any disclaimer, the term of this patent is extended or adjusted under 35 U.S.C. 154(b) by 300 days.

(21) Appl. No.: 15/854,486

(22) Filed: Dec. 26, 2017

(65) Prior Publication Data

US 2018/0185288 A1 Jul. 5, 2018

Related U.S. Application Data

(60) Provisional application No. 62/441,817, filed on Jan. 3, 2017, provisional application No. 62/470,324, filed on Mar. 12, 2017.

(51) Int. Cl.

| | |
|---|---|
| *A61K 9/14* | (2006.01) |
| *A61K 9/00* | (2006.01) |
| *A61K 9/08* | (2006.01) |
| *A61F 9/007* | (2006.01) |
| *A61K 31/43* | (2006.01) |
| *A61K 31/7048* | (2006.01) |
| *A61F 9/00* | (2006.01) |
| *A61K 31/7036* | (2006.01) |
| *A61K 47/38* | (2006.01) |

(52) U.S. Cl.
CPC ............ *A61K 9/146* (2013.01); *A61F 9/0008* (2013.01); *A61F 9/0017* (2013.01); *A61F 9/00727* (2013.01); *A61K 9/0048* (2013.01); *A61K 9/08* (2013.01); *A61K 9/14* (2013.01); *A61K 31/43* (2013.01); *A61K 31/7036* (2013.01); *A61K 31/7048* (2013.01); *A61K 47/38* (2013.01)

(58) Field of Classification Search
CPC ............................. A61F 9/0008; A61F 9/0017
See application file for complete search history.

(56) References Cited

U.S. PATENT DOCUMENTS

| | | | |
|---|---|---|---|
| 5,019,037 A | 5/1991 | Wang et al. | |
| 5,258,412 A * | 11/1993 | Peyman | ............... A61F 9/00 514/772 |
| 5,336,175 A * | 8/1994 | Mames | ............ A61F 9/00727 128/898 |
| 7,811,832 B2 | 10/2010 | Zacks et al. | |
| 8,343,931 B2 | 1/2013 | Zacks | |

(Continued)

FOREIGN PATENT DOCUMENTS

| | | |
|---|---|---|
| WO | WO2010/038004 A1 | 4/2010 |
| WO | WO2018/128876 A1 | 7/2018 |

*Primary Examiner* — Scott J Medway
*Assistant Examiner* — Dung T Ulsh
(74) *Attorney, Agent, or Firm* — Shay Glenn LLP

(57) ABSTRACT

A method of treating a detachment of a retina of an eye, the method including the steps of injecting a substance into a vitreous cavity of the eye, the substance slowing flow of fluid through the vitreous cavity into a subretinal space to reduce a rate of accumulation of a subretinal fluid in the subretinal space to below a rate of removal of the subretinal fluid from the subretinal space by retinal pigment epithelium; and permitting the retinal pigment epithelium to reattach the retina. The invention also includes devices for practicing the method.

31 Claims, 15 Drawing Sheets

(56) References Cited

U.S. PATENT DOCUMENTS

| | | |
|---|---|---|
| 9,192,650 B2 | 11/2015 | Zacks et al. |
| 9,549,895 B2 * | 1/2017 | Nakazawa ............ A61K 9/0048 |
| 9,724,357 B2 | 8/2017 | Vavvas et al. |
| 2004/0039253 A1 | 2/2004 | Peyman et al. |
| 2007/0014833 A1 * | 1/2007 | Milburn ................. A61K 31/56 424/427 |
| 2007/0038174 A1 | 2/2007 | Hopkins |
| 2011/0200676 A1 * | 8/2011 | Lin ........................... C08L 5/08 424/488 |
| 2012/0165783 A1 | 6/2012 | Wheatley et al. |
| 2014/0039456 A1 * | 2/2014 | Lerner .................... A61F 9/007 604/506 |
| 2014/0378888 A1 * | 12/2014 | Scherz .................... A61P 27/06 604/20 |
| 2016/0084853 A1 * | 3/2016 | Baldwin ................ G01N 33/74 424/134.1 |
| 2017/0135960 A1 * | 5/2017 | Yu ....................... A61K 31/5377 |
| 2018/0066022 A1 * | 3/2018 | Chalberg ........... A61K 48/0066 |
| 2019/0159930 A1 * | 5/2019 | Ang ........................ A61M 5/31 |

\* cited by examiner

Hydroxypropyl Methylcellulose (HPMC):

Hyaluronic Acid:

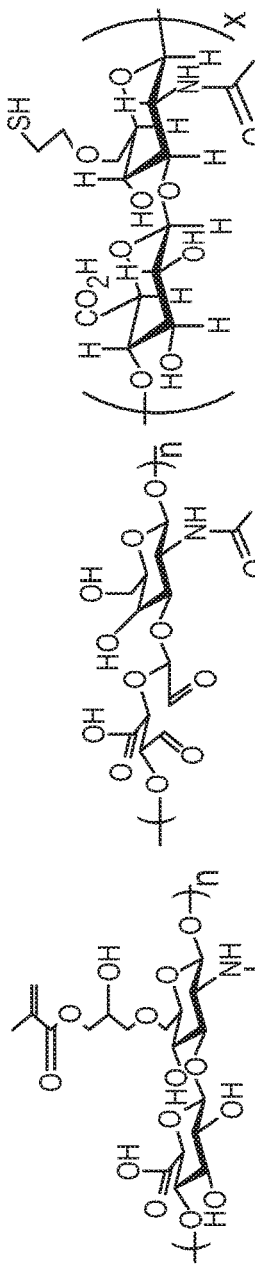
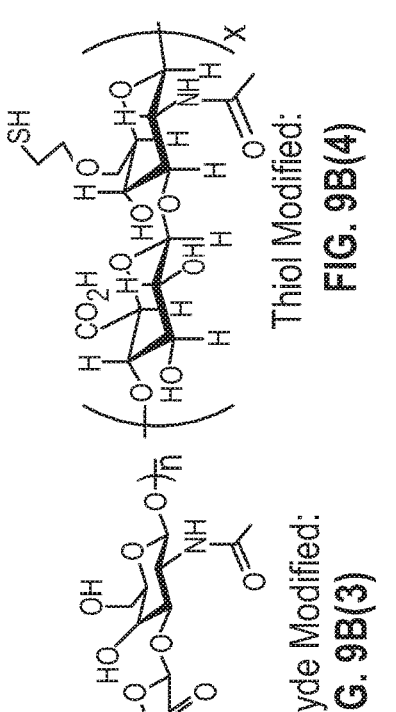
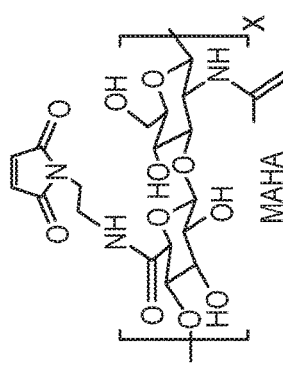
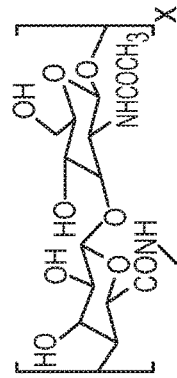
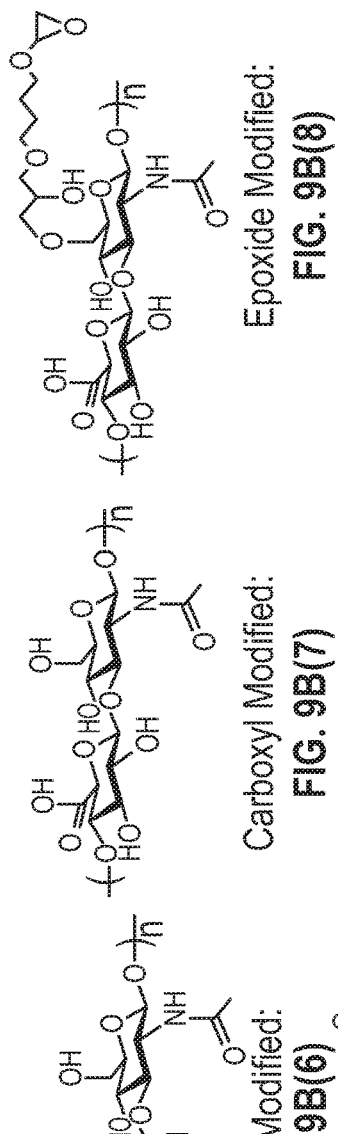
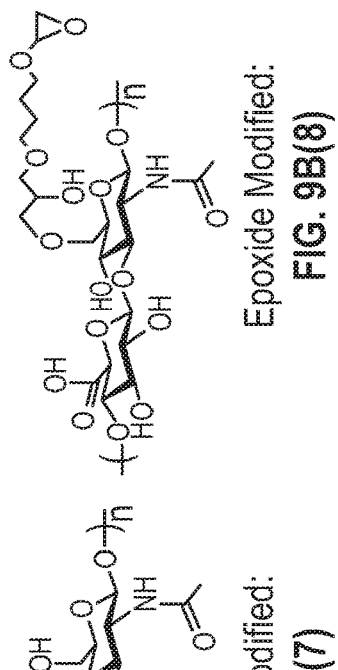
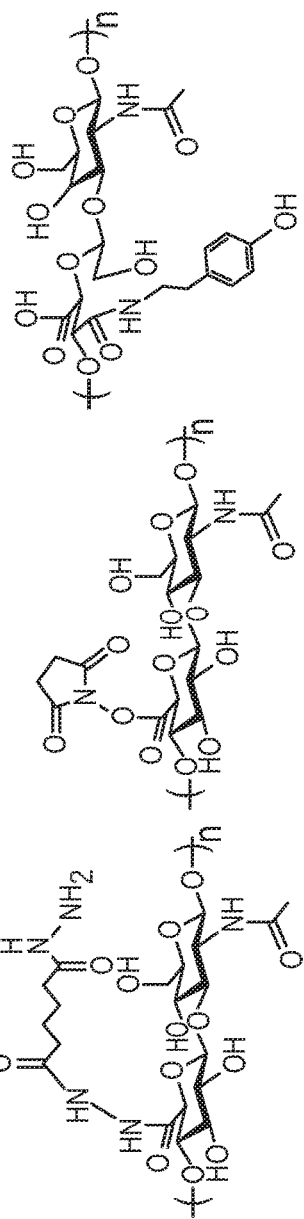
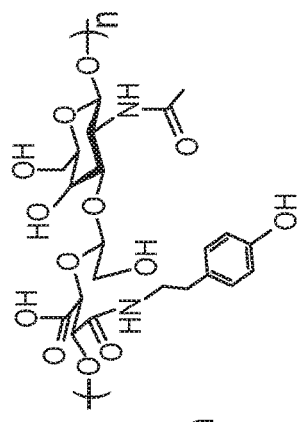
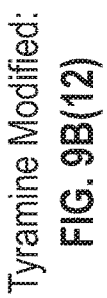
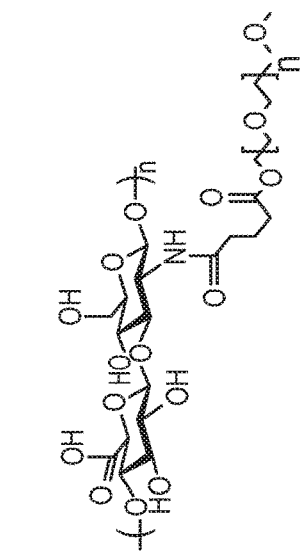
Maleimide Modified: FIG. 9B(1)
Methacrylate Modified: FIG. 9B(2)
Aldehyde Modified: FIG. 9B(3)
Thiol Modified: FIG. 9B(4)
Furan Modified: FIG. 9B(5)
Amine Modified: FIG. 9B(6)
Carboxyl Modified: FIG. 9B(7)
Epoxide Modified: FIG. 9B(8)
PEGylated Modified: FIG. 9B(9)
Hydrazide Modified: FIG. 9B(10)
NHS Ester Modified: FIG. 9B(11)
Tyramine Modified: FIG. 9B(12)

METHODS AND DEVICES FOR TREATING A RETINAL DETACHMENT

CROSS REFERENCE TO RELATED APPLICATIONS

This application claims the benefit of U.S. Application No. 62/441,817, filed Jan. 3, 2017, and U.S. Application No. 62/470,324, filed Mar. 12, 2017, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Retinal detachment is a vision threatening disease affecting approximately 1 in 10,000 people worldwide. While there are different causes of a retinal detachment, by far the most common type is due to a tear in the retina. This break in the integrity of the retina allows fluid from the anterior chamber to flow through the vitreous cavity to accumulate beneath the retina. Subretinal fluid is normally rapidly removed from the subretinal space by the retinal pigment epithelium. However, in some instances, flow through the tear in the retina and into the subretinal space exceeds the capacity of the retinal pigment epithelium to remove subretinal fluid. The result is increasing accumulation of subretinal fluid and a retinal detachment. Unrepaired, these types of retinal detachments uniformly lead to blindness.

Current approaches to repairing retinal detachments involves three fundamental steps. First, all retinal tears are identified. Second, the retina tears are sealed with a tamponade agent, preventing additional accumulation of subretinal fluid and allowing the retinal pigment epithelium to remove the existing fluid. Finally, permanent adhesions are formed around the retinal tears to prevent recurrent detachment.

The most common approach to repairing a retinal detachment involves invasive surgical procedures with success rates of approximately 80-85%. These invasive surgical procedures largely rely on filling the eye with either gas or silicone oil to seal the retinal tears. In some instances, it is possible to avoid an invasive surgical procedure by injecting a gas bubble into the vitreous cavity and positioning the patient such that the gas bubble seals the retinal tear.

Unfortunately, only certain types of retinal tears are candidates for this non-surgical procedure, which requires strict patient positioning and altitude restrictions, and is successful only 50% of the time. Fundamentally, the key component to retinal detachment repair is sealing the retinal break with a tamponade agent such as gas or oil.

SUMMARY OF THE DISCLOSURE

One aspect of the present invention relates to a non-intuitive, unexpected and unique approach to treating a retinal detachment by using a substance that when inserted into the vitreous cavity of an eye with a retinal detachment slows the diffusion of water and/or solutes through the vitreous cavity, and secondarily through the retina break, thereby reducing the rate of subretinal fluid accumulation. By sufficiently reducing the rate of subretinal fluid accumulation, fluid removal by the retinal pigment epithelium can outpace accumulation through the retinal tear. The result is reattachment of the retina without the need for a tamponade agent.

Another aspect of the invention are substances that can be injected or otherwise added to the vitreous cavity to slow the diffusion of water and/or solutes through the vitreous cavity. Yet another aspect of the invention is a device for injecting a powder or other dry mass into biologic tissue, such as the vitreous cavity of the eye.

One aspect of the invention provides a method of treating a detachment of a retina of an eye. In some embodiments the method includes the steps of injecting a substance into a vitreous cavity of the eye, the substance slowing flow of fluid through the vitreous cavity into a subretinal space to reduce a rate of accumulation of a subretinal fluid in the subretinal space to below a rate of removal of the subretinal fluid from the subretinal space by retinal pigment epithelium; and permitting the retinal pigment epithelium to reattach the retina. In some embodiments, the substance also slows flow of the fluid through a tear in the retina into the subretinal space.

Some embodiments of the method include the step of increasing a viscosity of the fluid in the vitreous cavity. The fluid may be, e.g., vitreous fluid or a fluid that has replaced natural vitreous fluid.

In some embodiments, the substance comprises a dry mass, such as, e.g., a powder.

In some other embodiments, the substance comprises hyaluronic acid formulated as a solution. The solution may have a hyaluronic acid concentration of, e.g., greater than 5% by weight, greater than 15% by weight, greater than 30% by weight, or any concentration in ranges between these concentrations. In some embodiments of the substance a therapeutic agent (e.g., a neuroprotective agent or an agent that inhibits photoreceptor cell death) can be included with the hyaluronic acid solution. In other embodiments, the substance comprises hyaluronic acid formulated as a dry mass.

In some embodiments, the substance comprises hydroxypropyl methylcellulose (HPMC) formulated as a solution with a concentration greater than 5% by weight, greater than 15% by weight, greater than 30% by weight, or any concentration in ranges between these concentrations. In other embodiments, the substance comprises hydroxypropyl methylcellulose (HPMC) formulated as a dry mass.

In some embodiments, injecting a substance comprises injecting a substance with a volume between 0.05 mL to 0.5 mL. Some such embodiments include the optional step of removing fluid from the eye prior to the injecting step.

In some embodiments, injecting a substance comprises injecting a substance with a volume between 0.05 mL to 0.2 mL. Such methods may optionally be performed without removing fluid from the eye prior to the injecting step.

In some embodiments, the substance has a viscosity of greater than 10,000,000 (cps) (resting) and 500,000 (cps) (dynamic).

In some embodiments, the injecting step includes the steps of inserting a needle into the vitreous cavity; and delivering the substance from a reservoir through the needle into the vitreous cavity. In some such embodiments, delivering step may include the step of moving a plunger within the reservoir. In embodiments in which the substance is a dry mass, the moving step may include the step of oscillating the plunger. In some such embodiments, the step of moving the plunger may include the step of actuating a linear actuator to deliver the substance at a controlled rate. In these embodiments, the substance may be, e.g., hyaluronic acid formulated as a solution with a concentration greater than 15% by weight or hyaluronic acid formulated as a dry mass.

Another aspect of the invention provides an apparatus for treating retinal detachment having a hollow needle with an opening at a distal end, the needle being sized and configured for insertion into a vitreous cavity of a human eye; a reservoir attached to a proximal end of the needle and in communication with an interior of the hollow needle; a plunger disposed within the reservoir; and an actuator configured to oscillate the plunger within the reservoir to deliver powder from the reservoir into the interior of the needle and through the opening of the needle. In some embodiments, the needle may be an ultrathin walled needle of 22-gauge or smaller. Some embodiments may also include an optional a locking element configured to prevent the needle from being separated from the reservoir.

In some embodiments, the actuator includes a screw conveyor. In some such embodiments, the screw conveyor may be driven by an electric motor. In some such embodiments, the screw conveyor may be driven by air pressure.

In some embodiments, the reservoir is configured to vibrate, rotate, or shake to prevent the substance from sticking to a wall of the reservoir. In some embodiments, the reservoir is configured to be detachable from a remainder of the apparatus. In some embodiments, the actuator includes a pneumatic actuator. In some embodiments, the actuator includes an electric field actuator.

Yet another aspect of the invention provides a method of preparing a liquid formulation of hyaluronic acid. In some embodiments, the method includes the steps of placing hyaluronic acid in a reservoir of a syringe; placing buffered saline in the reservoir; and passing a plunger through the hyaluronic acid and buffered saline. Some such embodiments include an optional step of removing the plunger from the syringe prior to the first placing step. Some embodiments add an additional optional step of placing a cap on an exit port of the reservoir prior to the first placing step. In some embodiments, the buffered saline includes phosphate. In some embodiments, the hyaluronic acid and the buffered saline are placed in the reservoir in relative quantities to create a 20-30% hyaluronic acid liquid formulation.

Still another aspect of the invention provides a method of preparing a liquid formulation of hyaluronic acid. In some embodiments, the method includes the steps of coupling an exit port of a first syringe containing hyaluronic acid to an exit port of a second syringe containing buffered saline; depressing a plunger of the first syringe or a plunger of the second syringe; thereafter, depressing the plunger of the other syringe; repeating the depressing steps to move the contents of the syringes between the syringes until a homogeneous hyaluronic acid liquid formulation is achieved; and separating the first syringe from the second syringe.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-B show the device of FIGS. 5A-C in use to deliver a substance to the vitreous cavity of an eye.

FIGS. 9A and 9B(1)-(12) provide examples of modifications of hyaluronic acid that can be used to practice embodiments of the retinal detachment treatment inventions described herein.

DETAILED DESCRIPTION

Figure 1A:
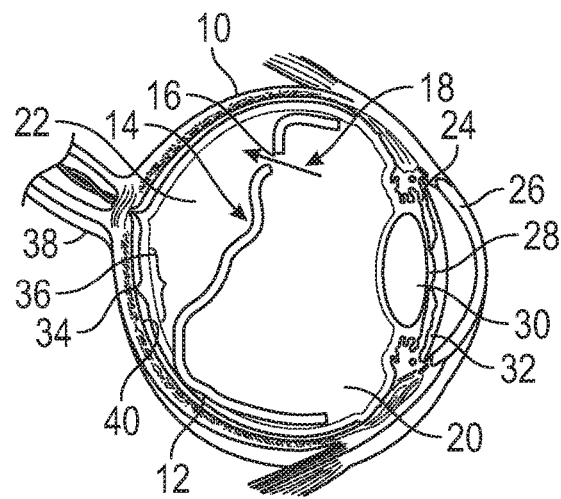
FIGS. 1A-D are schematic drawings showing a retinal detachment treatment method according to one embodiment of the invention.

The invention described and claimed herein broadly relates to any substance that is inserted into the vitreous cavity that alters one or more characteristics (e.g., viscosity) of the fluid in the vitreous cavity (e.g., natural vitreous or fluid that has replaced removed vitreous) to slow the diffusion of water and/or solutes through the vitreous cavity for the purpose of treating a retinal detachment. Current treatments of retinal detachments involve sealing a retinal break with a tamponade agent such as gas or silicone oil. The present invention fundamentally differs from traditional methods of retinal detachment repair. Instead of sealing the retinal break, the present invention instead reduces the flow of water and/or solutes through the vitreous cavity. The unexpected result is a reduced rate of subretinal fluid accumulation. Again, traditionally, all fluid flow through a break must be halted to cause retinal reattachment. However, the present invention challenges this orthodoxy by demonstrating that reductions in water and/or solute flow through the vitreous results in reattachment of the retina.

The present invention includes any substance that may be inserted into the vitreous cavity to slow diffusion of water and/or solute transport through the fluid (natural vitreous or fluid such as saline that has replaced natural vitreous) in order to treat a retinal detachment. Such substances include, but are not limited to, natural gums, starches, pectins, agar-agar, gelatin, mechanical and thixotropic agents, and fumed silica. Such substances can be any rheology modifier such as, but not limited to, polyurethanes, acrylic polymers, latex, styrene/butadiene, polyvinyl alcohol (PVA), cellulosics (cellulose acetate), cellulose triacetate, cellulose propionate, cellulose acetate propionate (CAP), cellulose acetate butyrate (CAB), nitrocellulose, cellulose sulfate, methyl cellulose, ethylcellulose, ethyl methyl cellulose, hydroxypropyl cellulose (HPC), hydroxyethyl methyl cellulose, ethyl hydroxyethyl cellulose, carboxymethyl cellulose (CMC), hydroxyl methylcellulose (HMC), hydroxylethyl cellulose, hydroxypropyl methylcellulose (HPMC), chemically modified cellulose macromolecules), sulfonates, gums (guar, anthan, cellulose, locust bean, acacia), saccarides (carrageenan, pullulan, konjac, alginate), proteins (casein, collagen, albumin), modified castor oil, organosilicones (silicone resins, dimethicones, modified silicones), synthetic hydrogels (polyvinyl alcohol, sodium polyacrylate, acrylate polymers and copolymers), organogels, xerogels, natural hydrogels (agrose, methylcellulose, hyaluronan, chondroitin sulfate), modified hydrogels, cross-linked hydrogels, polyionic polymers, and nanocomposite hydrogels. For any of the aforementioned substances, covalent or non-covalent modifications can be made to enhance their ability to slow the diffusion of water and/or solutes when placed in the vitreous cavity. Common covalent modifications that can be added to any of the aforementioned substances include, but are not limited to, maleimide addition, methacrylate addition, aldehyde addition, thiol addition, furan addition, amine addition, carboxyl addition, epoxide addition, PEGylation, hydrazide addition, NHS ester addition, and tryamine addition.

As described in more detail below, any of the aforementioned substances can be formulated into a liquid such as a solution, a suspension, a mixture, or a dry formulation for delivery into the vitreous cavity of the eye. In the case of a dry formulation, the dry formulation of the substance can be compacted with or without a biodegradable coating or coated in such a way to facilitate passage through a small gauge microtube or hollow bore needle.

In some embodiments, the formulations contain an additional active ingredient which serves a role distinct from the diffusion-slowing substance described about. In particular, ingredients which are designed to limit photoreceptor death, enhance visual recovery, or treat any other ocular condition may be added to the liquid formulation. For instance, inhibitors of apoptosis, such as, but not limited to, hydrophilic bile acids (UDCA or TUDCA), anti-FAS-ligand antibodies, MET12 or a fragment thereof, Faim2 or a fragment thereof, caspase inhibitors, or neuroprotective agents such as, but not limited to, MCP-1 antagonist, TNF-alpha antagonist, IL-1 beta antagonist, or a bFGF mimetic, may be ingredients added to limit the degree of photoreceptor death from the retinal detachment. Such ingredients are envisioned to be either proteins, peptides, small molecules, or combinations thereof and can be added to the original substance in its liquid or dry formulation. Some of the possible additional ingredients are described, e.g., in U.S. Pat. Nos. 7,811,832; 9,192,650; 8,343,931; 9,549,895 and 9,724,357.

In each of these cases, the ideal intravitreal injection volume ranges from 0.05 mL to 0.2 mL. Higher injection volumes up to 0.5 mL are possible, but fluid must be removed from the anterior chamber to prevent excessive intraocular pressure elevations and therefore add a level of complexity and risk to the procedure.

The amount of substance delivered to the vitreous cavity must also be sufficient to slow the diffusion of water and/or solute flow throughout the vitreous cavity, which has a total volume of approximately 5 mL. Since the ideal injection volume is $1/40$ to $1/100$ the volume of the entire vitreous cavity, delivering sufficient quantities of a substance to cause a reduction in diffusion of water and/or solutes throughout the vitreous cavity requires exceedingly high formulation concentrations, far exceeding what has been attempted previously or is available commercially.

Beyond the challenges of creating such high concentration formulations, these formulations pose major delivery challenges. While intraocular delivery through microneedles of 22-gauge or smaller can be performed in the clinic setting, anything larger requires surgical wound closure. Because of the small delivery volumes and subsequent the high concentration requirements, even standard 22-gauge needles are not sufficiently large to allow delivery of these substances due to their high formulation viscosities of greater than 10,000,000 (cps) (resting) and 500,000 (cps) (dynamic).

In the case of a dry powder formulation, no device currently exists to deliver a dry formulation through a microneedle to biologic tissue. Accordingly, the present invention includes unique delivery methods to deliver these high concentration substances. The inventions described and claimed herein also broadly relate to a device capable of delivering a dry mass formulation of a substance into a biologic tissue, including but not limited to the eye. The device uses a method of pushing or carrying the dry formulation of the substance into the biologic tissue of interest. The device can be used to deliver the dry formulation of a substance into an eye with a rhegmatogenous retinal detachment with the purpose of slowing the flow of water and/or solutes through the vitreous cavity, and secondarily across a retinal break, thereby reducing the accumulation of subretinal fluid and allowing the retinal pigment epithelium to reattach a detached retina.

In the case of a solution, suspension, or mixture, specially designed ultrathin walled microneedles are provided to allow delivery into the eye without requiring surgical wound closure. In some embodiments, this is a microneedle no larger than 22-gauge, e.g., ranging from 23-guage to 32-gauge. To advance the specific formulation of the aforementioned substance through the microneedle, either a manual force, a mechanical force, or combination thereof can be applied.

A linear actuator may also be used to provide a controlled delivery of the high formulation substance through one of these specially designed microneedles. For a dry formulation, a specialty designed linear actuator or screw type conveyer is envisioned which advances the dry formulation down the needle shaft and into the vitreous cavity.

Figure 1B:
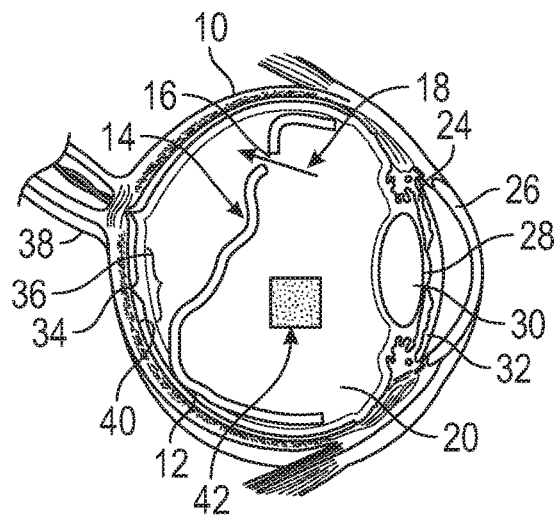
Figure 1C:
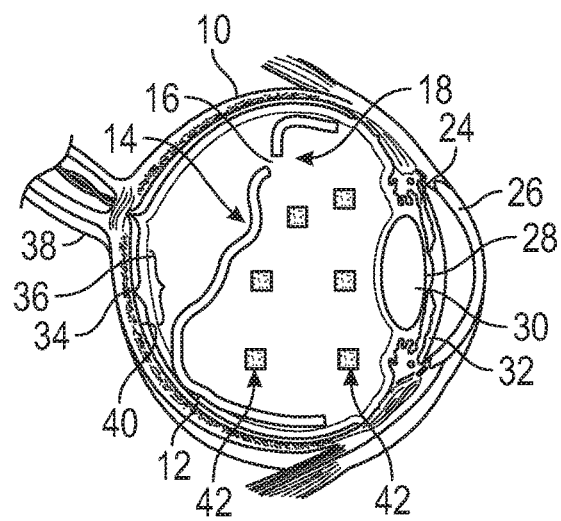
Figure 1D:
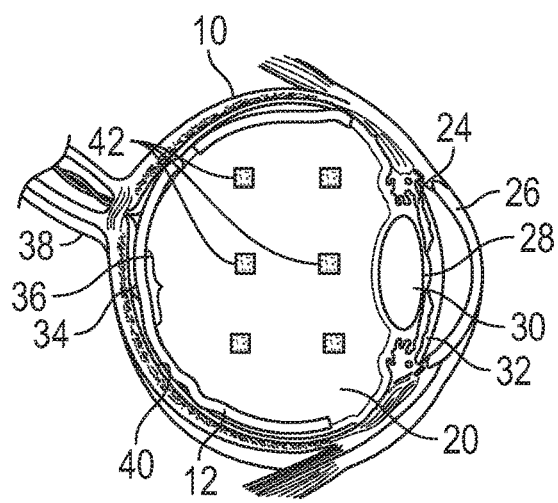

FIGS. 1A-D are schematic drawings illustrating a retinal detachment treatment method according to one embodiment of the invention. FIG. 1A shows an eye 10 with a retina 12 that has a detached area 14 due to a break or tear 16 in the retina that allows fluid flow 18 from the vitreous cavity 20 into the subretinal space 22. Also shown in this figure are the iris 24, cornea 26, pupil 28, lens 30, iris 32, fovea 34, macula 36, optic nerve 38 and subretinal epithelium 40. In FIG. 1B, a substance 42 that slows fluid and/or solute transport through the vitreous cavity 20 has been inserted into the vitreous cavity 20. As the substance 42 distributes throughout the vitreous cavity 20, it reduces flow through the vitreous cavity 20, and secondarily through the retinal break 16 and into the subretinal space 22, as shown in FIG. 1C. The reduction in flow through the vitreous cavity and secondarily through the retinal break 16 allows the cells of the retinal pigment epithelium 40 to remove the subretinal fluid thereby reattaching the retina 12, as shown in FIG. 1D.

Figure 2:
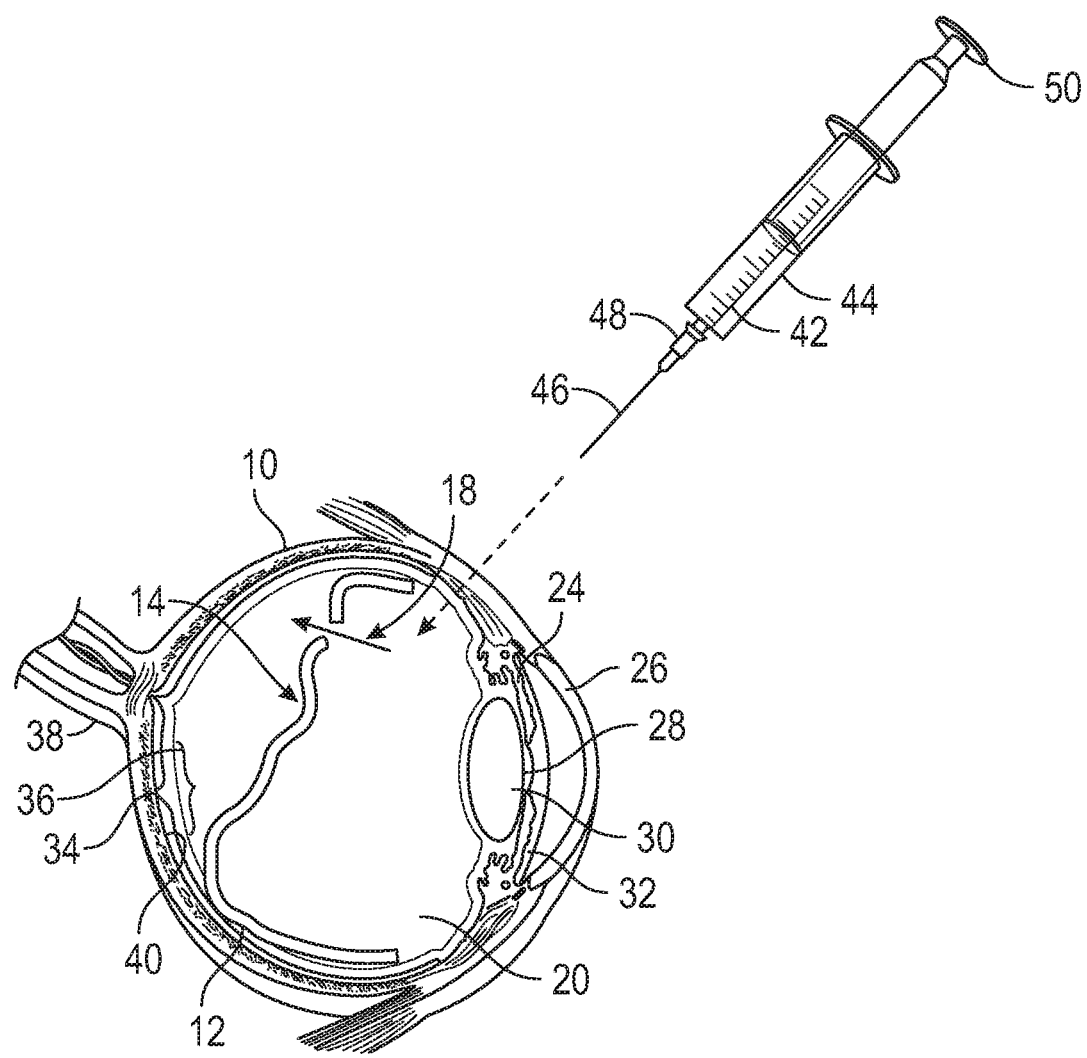
FIG. 2 illustrates an embodiment of a device that may be used to practice the method illustrated by FIGS. 1A-D.

FIG. 2 illustrates an embodiment of a device that may be used to practice the method illustrated by FIGS. 1A-D. In this embodiment, the substance 42 is a liquid that, when injected into the vitreous cavity, slows diffusion of water and/or solutes through the vitreous cavity. A syringe 44 containing the liquid form of the substance 42 is attached to an ultrathin-walled needle 46 through a locking system 48 to prevent the needle from being pushed off. The needle 46 is then inserted into the vitreous cavity 20 through the pars plana of the eye. The plunger 50 is advanced either manually or mechanically to push the liquid form of the substance 42 through the ultrathin walled needle 46 and into the vitreous cavity 20.

Figure 3B:
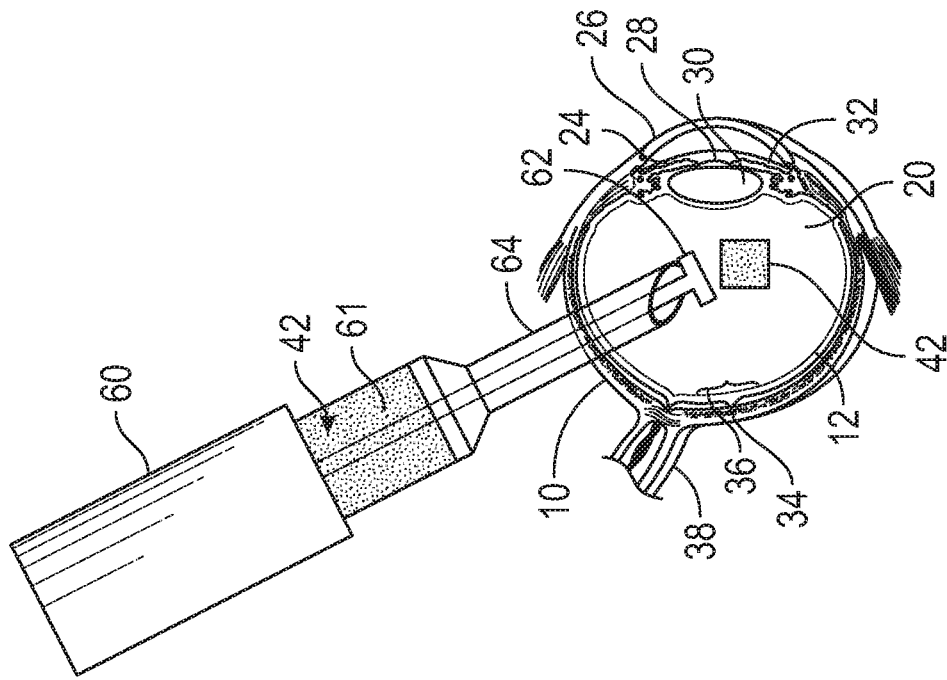
FIGS. 3A-B illustrate another embodiment of a device that may be used to practice the method illustrated by FIGS. 1A-D.
Figure 3A:
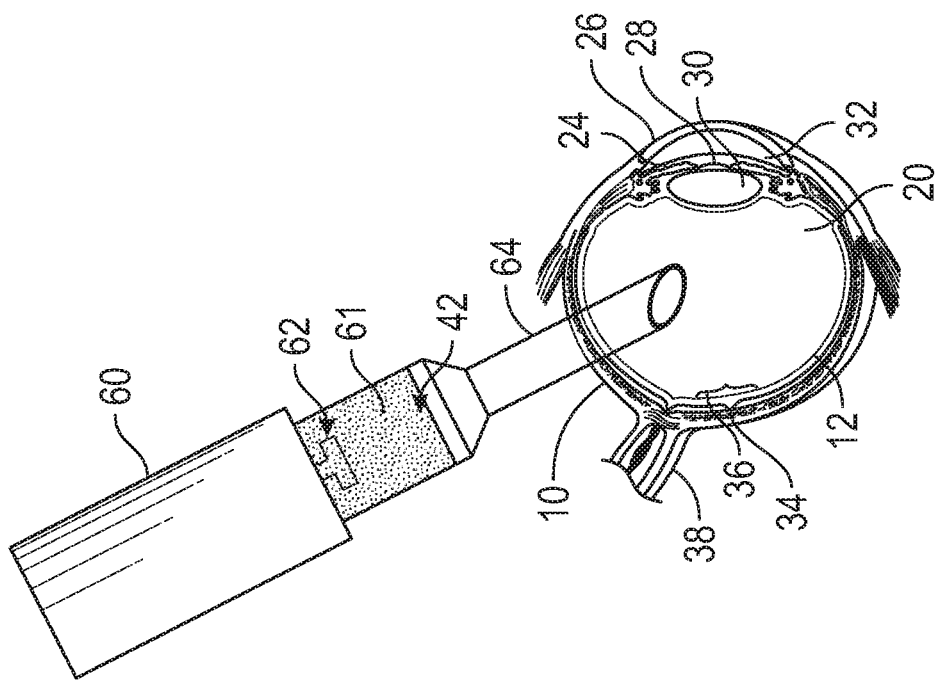

FIGS. 3A-B illustrate another embodiment of a device that may be used to practice the method illustrated by FIGS. 1A-D. In this embodiment, the substance is a dry mass form of the substance 42 that slows diffusion of water and/or solutes through the vitreous cavity 20. As shown in FIG. 3A, a linear actuator 60 is attached to a plunger 62 that is in a withdrawn state. The plunger resides in a reservoir 61 containing a dry mass form of a substance and is connected to a hollow bore needle 64 that is inserted into the vitreous cavity 20 of the eye 10. The linear actuator 60 advances the plunger 62 and moves the dry mass form of the substance 42 from the reservoir 61 through the hollow bore needle 64 and into the vitreous cavity 20. The plunger 62 is then withdrawn by the linear actuator 60, and the process is repeated until a desired quantity of dry mass 42 has been delivered to the vitreous cavity 20 of the eye 10.

The reservoir 61 may be designed to hold a predetermined quantity of substance formulated into a dry mass. The reservoir can be made of any of the materials or combination of materials listed below. In some embodiments, the reservoir can have a valve or port (not shown) to facilitate filling with the substance to be injected in the biologic tissue. In some embodiments, the reservoir can have a filter (not shown) to remove bacterial contaminants. In some embodiments, the reservoir can have an opening (not shown) that allows for removal of water such that a hydrated substance can be placed in the reservoir and then the water removed to create a dry mass formulation. In some embodiments, the reservoir can be coated to prevent the substance from sticking to the walls of the reservoir. In some embodiments, the reservoir can vibrate, rotate, or shake to prevent the substance from sticking to the walls of the reservoir or enhance delivery of material into the hollow needle. In some embodiments, the reservoir can be transparent to allow for manual inspection of the quantity of substance that is left in the device. In some embodiments, the reservoir can be detachable from the remainder of the device.

In various embodiments, the needle or other hollow tube attached to the reservoir can be any length. The hollow tube can be made out of any material, have any bevel design, be sharp or dull, and/or have ultrathin walls. The hollow tube can be fixated to the reservoir through any number of means, including a Luer-lock or other screw type locking system.

In various embodiments, different methods of linear actuation may be used. These include, but are not limited to, mechanical, hydraulic, pneumatic, air cylinder, piezoelectric, electro-mechanical, solenoid, linear motor, telescoping linear actuator, wax motor, segmented spindle, moving coil, or moving iron controllable actuator (MICA). The driver of the actuation can be entirely contained within the handpiece, or it may require a connection to a separate piece of machinery, such as a generator, a driver, a motor, or an air compressor. For instance, in the case of a pneumatic actuator, the handpiece can be connected to an air compressor. The actuator can be powered by human generated energy or electrical energy. The electrical energy can come from a battery (either contained within the handpiece or externally connected), a generator, or a wall outlet supplying either alternating or direct current.

Another method of moving a dry form of a substance through a hollow tube is using a linear conveyor. A number of linear conveyors are envisioned. These include, but are not limited to slat/apron, ball transfer, belt, beltless magnetic, bucket, chute, drag/chain/tow, pneumatic/vacuum, powered roller, roller, vertical, vibrating, walking beam, and screw. A screw conveyor includes those with and without a central shaft. Types of screw conveyors include, but are not limited to, standard pitch, short pitch, half pitch, long pitch, variable pitch, double flight, tapered, single cut-flight, cut and folded flight, single flight ribbon, standard pitch with paddles, and paddles.

A number of methods of controlling the rate of delivery of the substance to the biologic tissue are envisioned. These include, but are not limited to, manual control, automated control, and combined manual/automated control. Manual control can rely on input from the user via voice or touch, including hand or foot control. Automated control may or may not use active feedback based on features of the device such as the quantity of substance remaining in the reservoir.

A number of materials can be used to construct the device, including metals, plastics, ceramics, and/or composites. The types of metals include, but are not limited to stainless steel, cobalt based alloys (Co—Cr—Mo, Co—Ni—Cr—Mo), titanium-based alloys (e.g., CP—Ti, Ti—Al—V, Ti—Al—Nb, Ti—13Nb—13Zr, Ti—Mo—Zr—Fe), tantalum, Ni—Ti, gold alloys, silver alloys, platinum, Pt—Ir. The types of plastics include, but are not limited to FEP, PFA, ETFE, PEEK, PE, KYNAR, Polyimide, Polyethylene (PE), high density polyethylene (HDPE), Polypropylene, PFA, Polyacetal, Polycarbonate, Polymethylpentene, polypropylene, polypropylene copolymer, Polysulfone, Poly(methyl methacrylate) (PMMA), PTFE, Silicone, and Viton. The types of ceramics include, but are not limited to, alumina, zirconina, carbon, bioactive glasses, porcelain. The types of composites include, but are not limited to, BIS-GMAquartz/silica and PMMA-glass fillers. The present invention can be a combination of one or more of the previously listed materials. Those materials that can be sterilized with either steam, heat, gas, chemical, or irradiation are preferred, though this is not a requirement for the present invention. The specific type of material chosen is not a key feature of the present invention. It is therefore likely that those skilled in the art could easily identify additional materials that could be used for the present invention. Any material that is used for the construction of the present device is therefore part of the present disclosure.

Figure 4A:
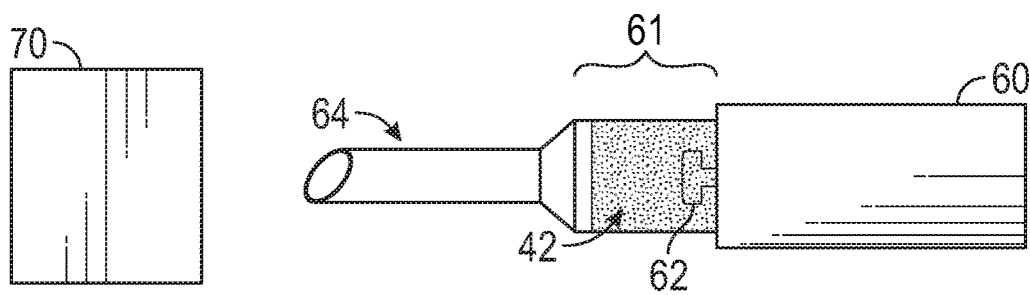
FIG. 4A-D illustrate the embodiment of FIGS. 3A-B in use to inject a dry mass form of a substance into biologic tissue.
Figure 4B:
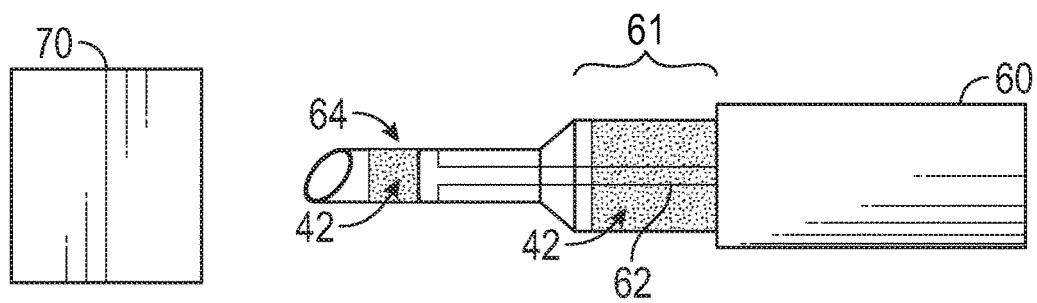
Figure 4C:
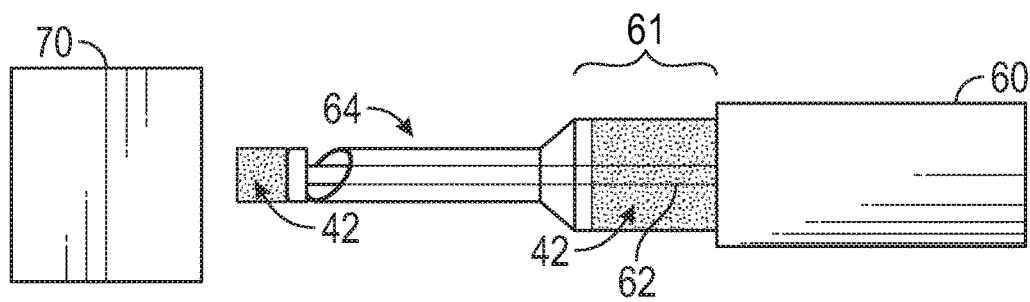
Figure 4D:
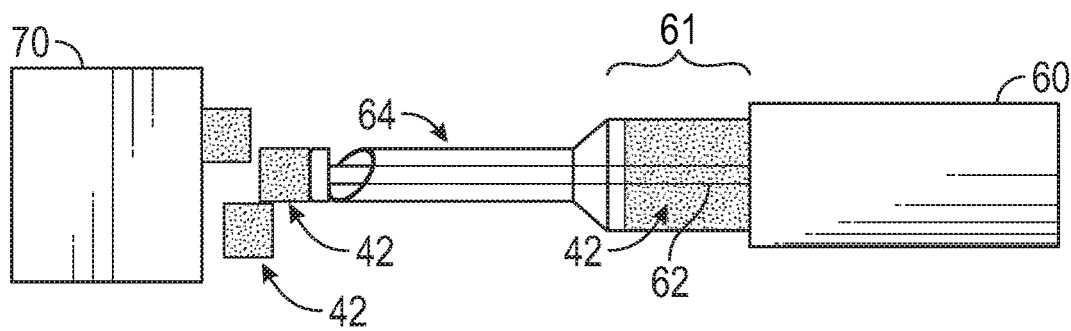

FIGS. 4A-D illustrate the embodiment of FIGS. 3A-B in use to inject a dry mass form of a substance 42 into biologic tissue 70. A linear actuator 60 is attached to a plunger 62 in its withdrawn state, as shown in FIG. 4A. The plunger 62 sits within a reservoir 61 containing a dry mass form of a substance 42. The reservoir 61 is attached to a hollow bore needle 64 which is inserted into a biologic tissue 70. As shown in FIG. 4B, as the linear actuator 60 advances the plunger 62, the dry mass 42 is moved from the reservoir 61 down the hollow bore needle 64. The linear actuator 60 eventually moves the plunger 62 to the end of the hollow bore needle 64. thereby delivering the dry mass form of a substance 42 into the biologic tissue 70, as shown in FIG. 4C. This process is repeated until a desired quantity of dry mass 42 is delivered to the biologic tissue 70.

Figure 5A:
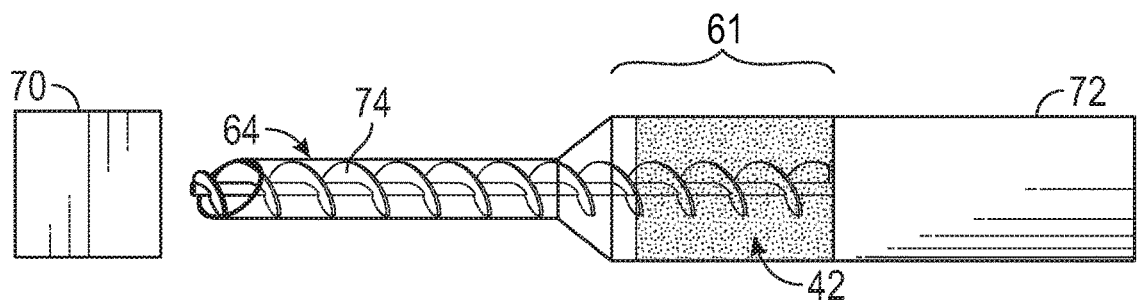
FIGS. 5A-C and 6A-B illustrate another embodiment of a device that can be used to deliver a substance to the vitreous cavity of the eye or to other biologic tissue.
Figure 5B:
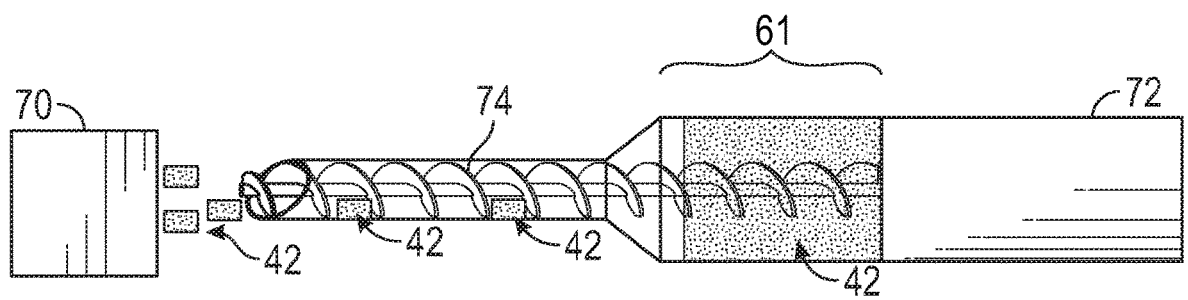
Figure 5C:
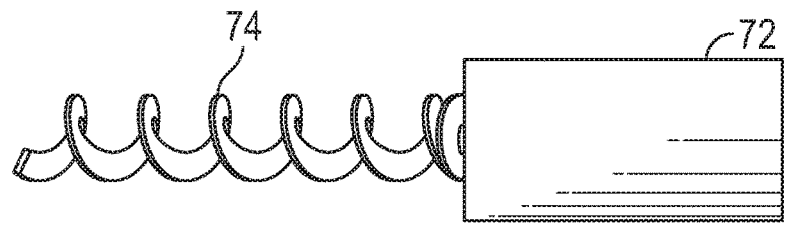
Figure 6B:
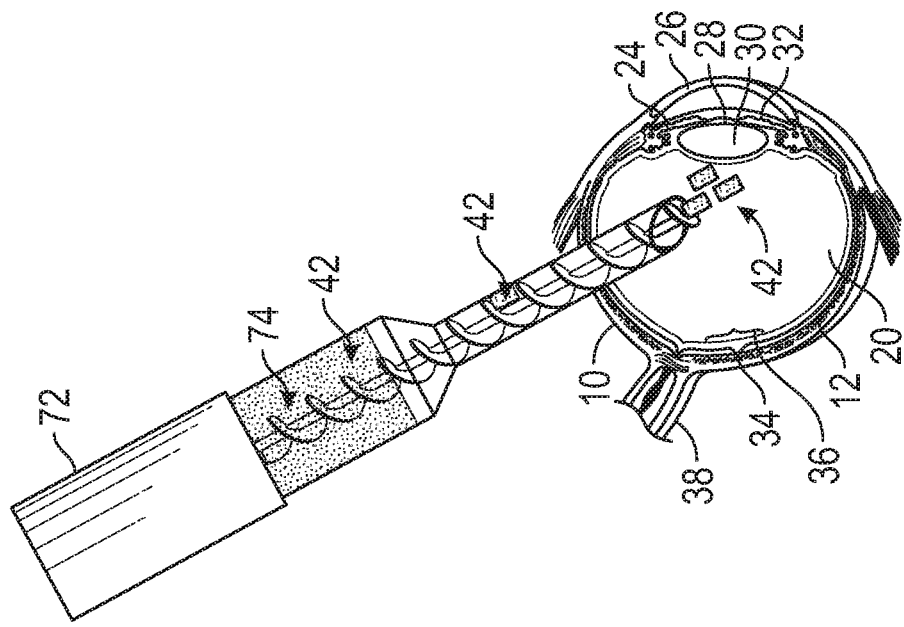
Figure 6A:
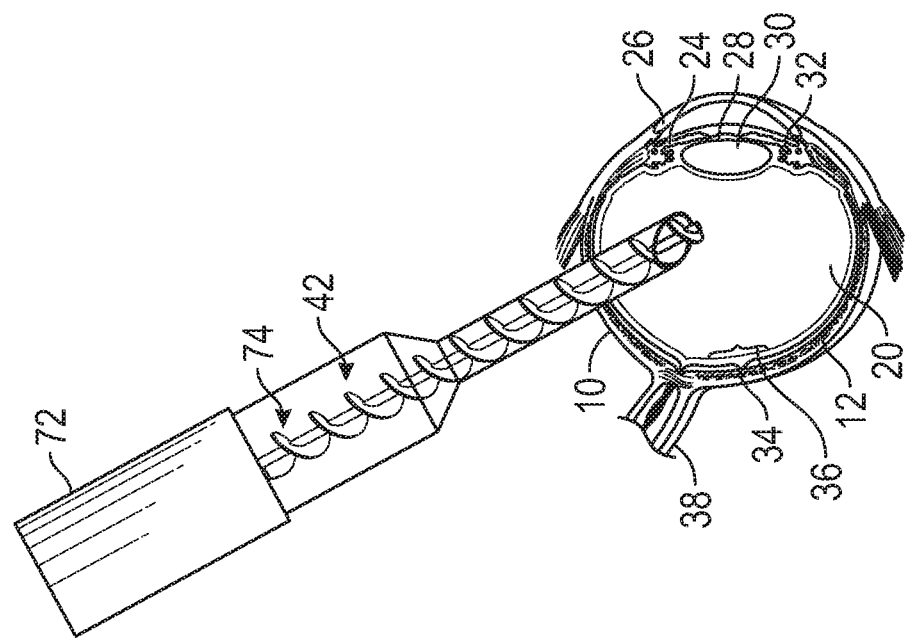

FIGS. 5A-C and 6A-B illustrate another embodiment of a device that can be used to deliver a substance (such as a dry mass or powder) to the vitreous cavity of the eye or to other biologic tissue to, e.g., practice the retinal detachment repair method described above. A motor 72 is attached to a screw conveyor 74 that sits within a reservoir 61 filled with a dry mass form of a substance 42. Motor 72 is connected to a hollow bore needle 64 inserted into a biologic tissue 70. As the screw conveyor 74 is rotated by the motor 72, dry mass is moved from the reservoir 61 through the needle 64 into the biologic tissue 70. Rotation of the screw conveyor 74 is continued until a desired quantity of dry mass 72 is delivered into the biologic tissue 70. The screw conveyor can have a shaft, as shown in FIGS. 5A-B or it can be shaftless, as shown in FIG. 5C. As before, the biologic tissue can be the vitreous cavity 20 of the eye 10, as shown in FIGS. 6A-B.

Figure 7:
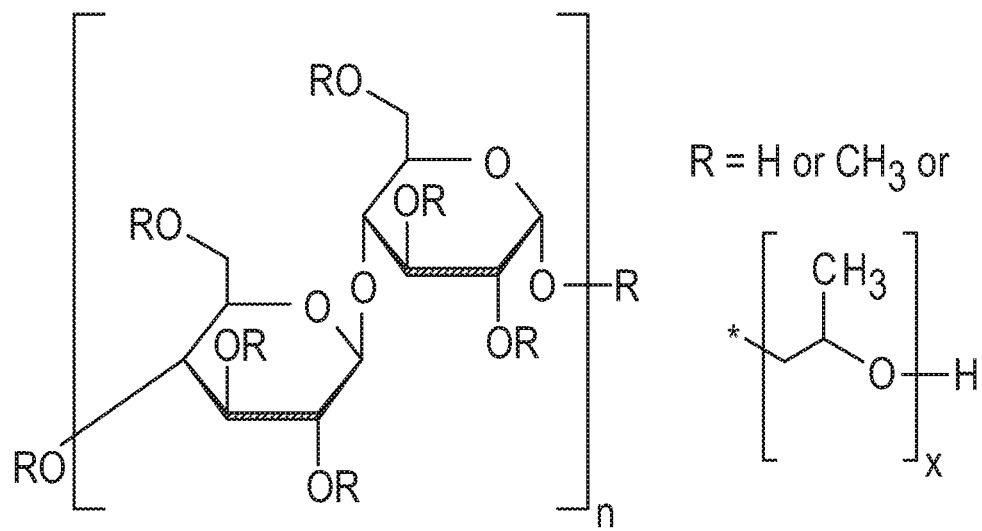
FIG. 7 is an example of a substance that can be inserted into the vitreous cavity of the eye to practice embodiment of the retinal detachment treatment inventions described herein.
Figure 8:
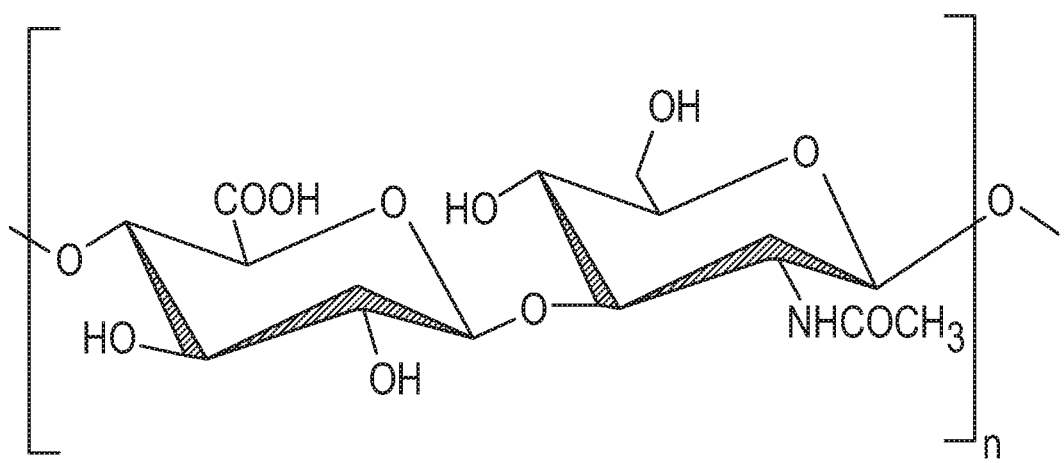
FIG. 8 is another example of a substance that can be inserted into the vitreous cavity of the eye to practice embodiments of the retinal detachment treatment inventions described herein.

FIGS. 7 and 8 are examples of substances that can be injected or otherwise inserted into the vitreous cavity of the eye to slow the diffusion of water and/or solutes through the vitreous cavity to practice the retinal detachment treatment inventions described above. Hydroxypropyl Methylcellulose (HPMC) is shown in FIG. 7. This substance can be delivered as either a highly concentrated liquid formulation or a dry formulation. HPMC is a semisynthetic polymer that acts as an emulsifier and thickening agent with good biocompatibility. Its primary use is in artificial tears or to temporarily protect the corneal endothelium during cataract surgery. It has never been used or described as a substance capable of repairing a retinal detachment through the novel mechanism of reducing the flow of water and/or solutes through the vitreous cavity. In order to use HPMC for this unique indication, much higher concentrations of HPMC must be developed that are greater than 5% by weight, with an ideal formulation of 15% or 30%. Dry formulations are also envisioned. These formulations greater than 5% by weight far exceed those that have been previously created and far exceed those in commercial use. As has been previously described, such formulations required specialty designed ultrathin walled needles. Or, in the case of a dry formulation, requires a novel device to deliver the dry formulation down the shaft of a microtube or needle into the vitreous cavity.

Hyaluronic Acid (HA) is shown in FIG. 8. This substance can be delivered as either a highly concentrated liquid formulation or a dry formulation. It is a natural polymer composed of the repeating disaccharides D-glucuronic acid and N-acetyl-D-glucosamine with chain lengths ranging from 5,000 Da to 20,000,000 Da. Hyaluronic acid has a long history of biocompatibility inside the human body as a surgical adjunct during cataract surgery, as a dermal filler for cosmetic procedures, and as an intra-articular injection to slow the effects of osteoarthritis. In each of these instances, hyaluronic acid is formulated as a solution ranging from 0.3% to 3% by weight. Higher formulations have not been developed due to formulation challenges, complexities in delivering these higher concentrations to target tissues, and a lack of clinical indications that would benefit from such higher concentrations.

In order to use hyaluronic acid to slow the flow of water and/or solutes to treat a retinal detachment, much higher concentrations of hyaluronic acid must be developed that are greater than 5% by weight, with an ideal formulation of 20% or 30%. Dry formulations are also envisioned. These formulations greater than 5% by weight far exceed those that have been previously created and far exceed those in commercial use. Delivery of these high concentrations of hyaluronic acid, such as 20% or higher solutions by weight, is also impossible through standard microneedles of 22-gauge or smaller due to the extremely high viscosity of these solutions. The high concentrations of hyaluronic acid needed for this novel method of treating a retinal detachment require specially designed ultrathin wall microneedles to prevent obstruction of the needle during injection into the vitreous cavity. And, in the case of a dry formulation, they require a specially constructed device which advances the dry hyaluronic acid down the shaft of the needle.

Figure 9A:
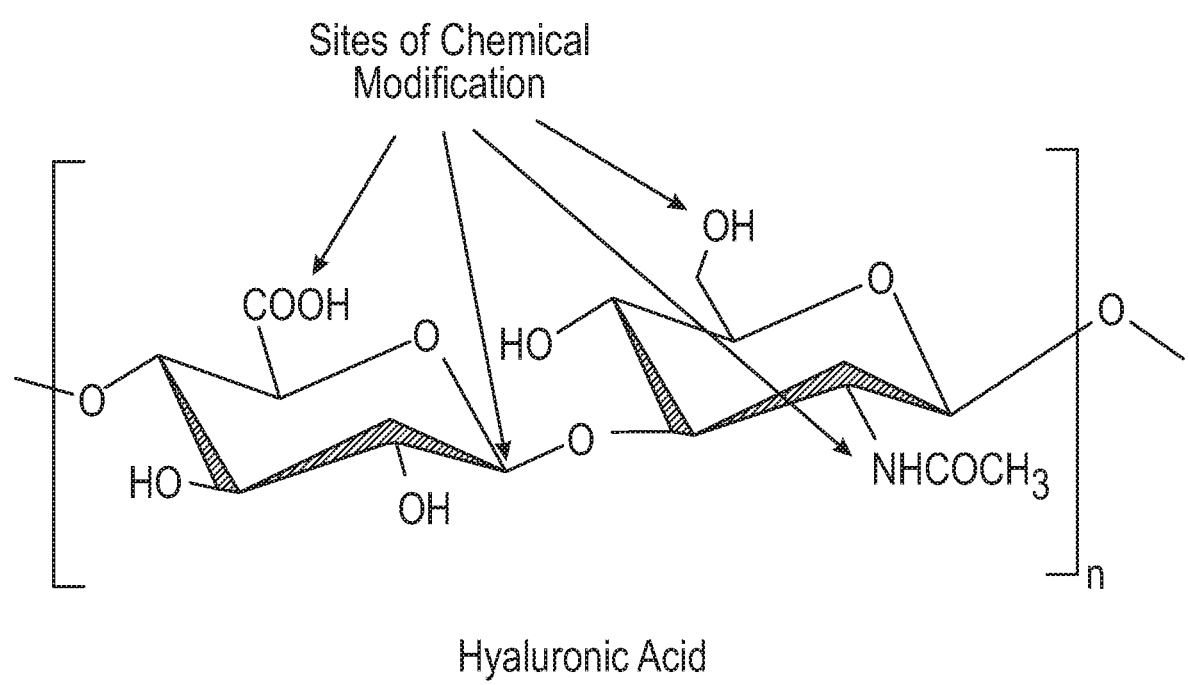

FIGS. 9A and 9B(1)-(12) provide examples of modifications of hyaluronic acid that can be used to enhance the effect of that substance in slowing diffusion of water and/or solutes through the vitreous cavity when injected or otherwise inserted into the vitreous cavity to practice the retinal detachment treatment inventions described above.

One example of a method and device to treat and repair a retinal detachment is as follows. High molecular weight hyaluronic acid is desiccated to create a fine powder. The powder is loaded into a reservoir. A 23-gauge ultra-thin walled needle is attached to one end of the reservoir. To the other end of the reservoir is a plunger attached to a pneumatic linear actuator. The pneumatic linear actuator can be detached from its control module and air pump to allow for sterilization. The pneumatic actuator, reservoir containing hyaluronic acid, and 23-gauge needle are sterilized. The pneumatic actuator is then attached to an air pump using filtered air to prevent bacterial contamination. The pneumatic actuator oscillates at a rapid rate. A pedal attached to a control module starts the pneumatic actuation. In a patient with a rhegmatogenous retinal detachment, the 23-gauge needle is inserted into the vitreous cavity. The pedal is depressed and the pneumatic actuator serially pushes small amounts of dry high molecular weight hyaluronic acid from the reservoir into the vitreous cavity. This process is continued until sufficient hyaluronic acid has been delivered to the vitreous cavity to reduce flow through the vitreous, and secondarily across the retinal break, thereby allowing the retinal pigment epithelium to remove the subretinal fluid and reattach the retina. An embodiment can use a screw conveyor instead of a pneumatic actuator to move dry high molecular weight hyaluronic acid from the reservoir to the vitreous cavity of the eye.

Figure 10:
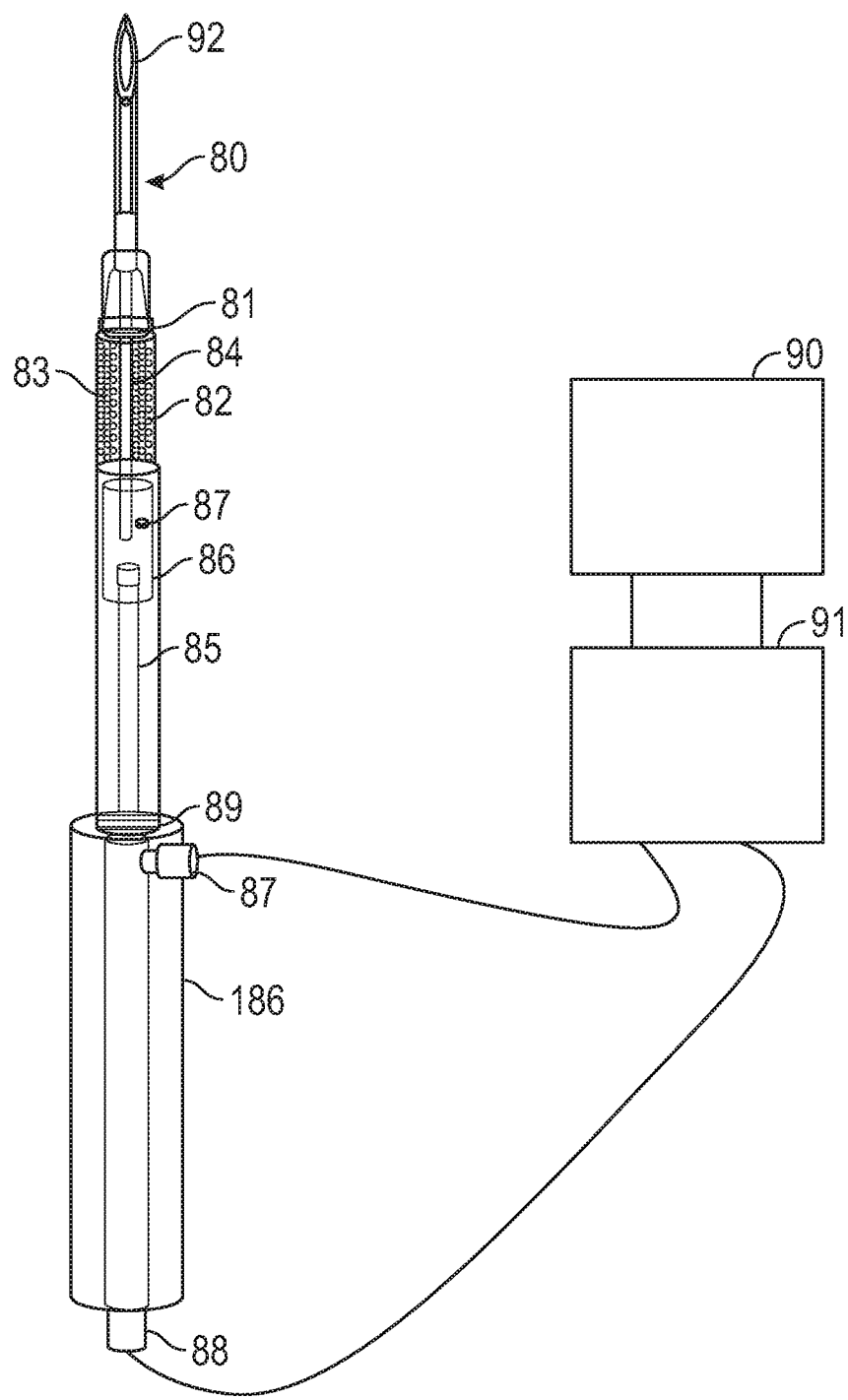
FIG. 10 shows yet another embodiment of a device for delivery of a dry mass to biologic tissue according to embodiments of the invention.
Figure 11A:
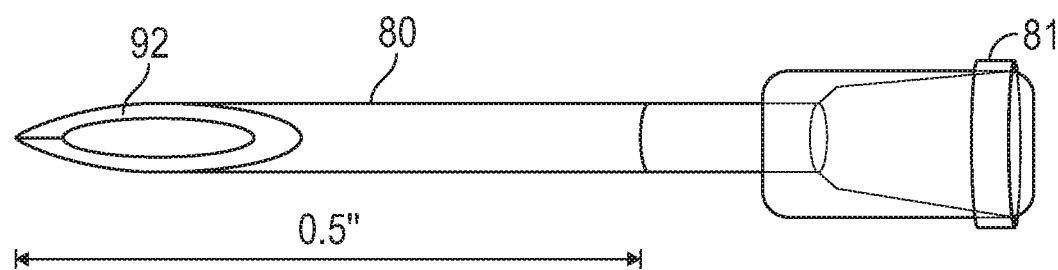
FIGS. 11A-B show details of the device of FIG. 10.
Figure 11B:
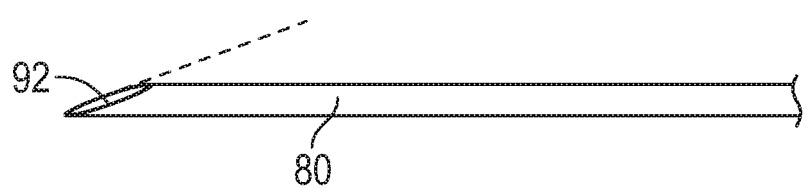

FIGS. 10-11 show yet another embodiment of a device for delivery of a dry mass to biologic tissue according to this invention. In this embodiment, the device has a 23 gauge ½ inch long ultrathin walled hypodermic needle 80 attached via a luer lock 81 to a reservoir 82 containing the dry mass powder 83, such as hyaluronic acid as described above. A push rod 84 (e.g., 0.018 inch diameter 316 tempered stainless steel) extends through the reservoir 82 into needle 80, as shown. The push rod 84 is attached to an air cylinder plunger 85 via a coupler 86 and set screw 87. Plunger 85 is attached via mounting threads 89 to an air cylinder 186 (e.g., 5/16 inch bore stainless steel) that alternately admits and exhausts compressed air from a compressor 90 under the control of a controller 91 operating valves (not shown) via inlet/exhausts 87 and 88 to oscillate plunger 85, e.g., in two inch strokes six times per second to move portions of the powder 83 from the reservoir through the needle 80 into biologic tissue, such as the vitreous cavity of the eye. In some embodiments, the wall thickness of needle 80 may be less than 0.005 inches, or 0.002-0.003 inches. In some embodiments, needle 80 may have an outer diameter of 0.0255-0.0260 inches, an inner diameter of 0.0200-0.0215 inches and a 40-60% bevel at the tip 92. NOW silicone MDX 4159 may be applied to the surface of the needle.

Figure 12:
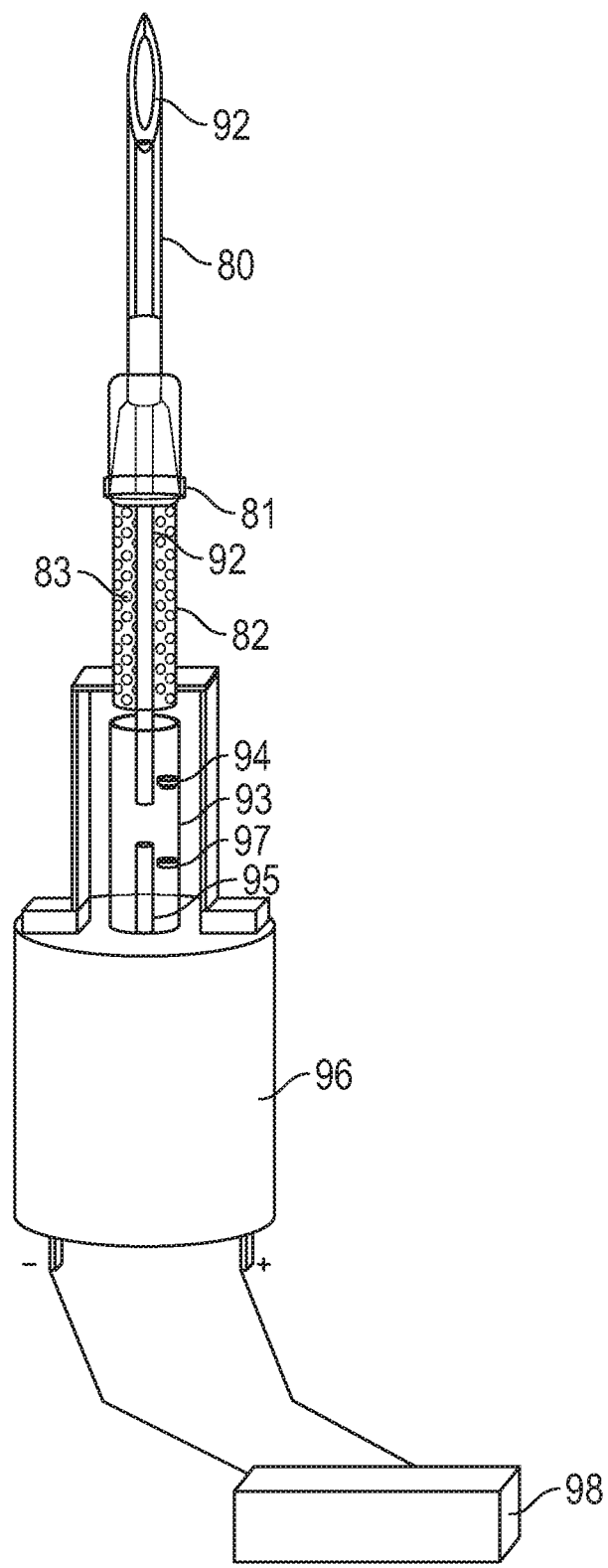
FIG. 12 shows yet another embodiment of a device for delivery a dry mass to biologic tissue according to embodiments of this invention.

FIG. 12 shows yet another embodiment of a device for delivery a dry mass to biologic tissue according to this invention. In this embodiment, the device has a 23 gauge ½ inch long ultrathin walled hypodermic needle 80 attached via a luer lock 81 to a reservoir 82 containing the dry mass powder 83, such as hyaluronic acid as described above. A threaded rod 92 (e.g., 0000-160#303 stainless steel) extends through the reservoir 82 into needle 80, as shown. Threaded rod 92 is connected via a set screw 94 to a motor shaft coupler 93, which is attached to a shaft 95 of a permanent magnet DC motor 96 (e.g., 18,000 rpm or more) via a set screw 97. A power supply 98 powers the motor 96. The motor 96 turns to advance threaded rod 92 to move portions of the powder 83 from the reservoir through the needle 80 into biologic tissue, such as the vitreous cavity of the eye.

Figure 13A:
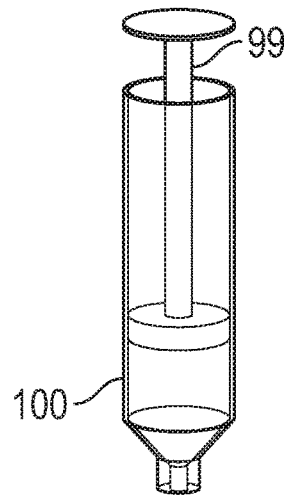
FIGS. 13A-E show a method of compounding a liquid formulation of 20% hyaluronic acid.
Figure 13B:
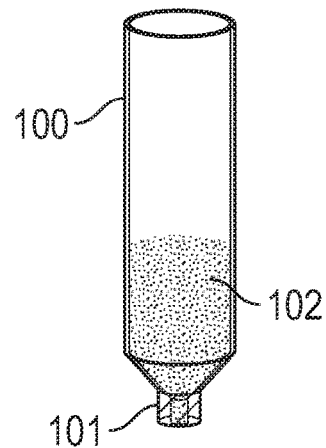
Figure 13C:
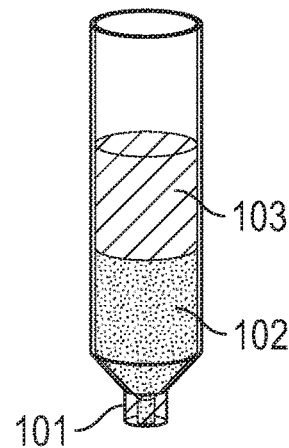
Figure 13D:
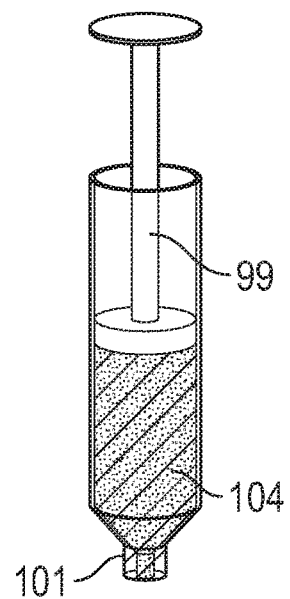
Figure 13E:
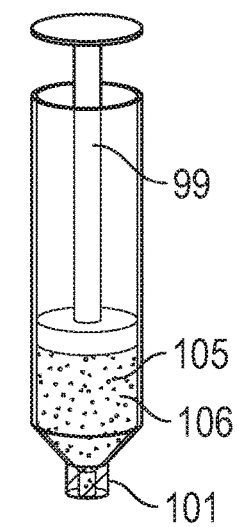

FIGS. 13A-E show a method of compounding a liquid formulation of 20% Hyaluronic Acid. In this method, the plunger 99 from a syringe 100 is removed, as shown in FIG. 13B. A locking syringe cap 101 is placed on the syringe 100 and the barrel of the syringe is filled with 1.0 grams of hyaluronic acid 102. Phosphate buffered saline 103, or any compatible ocular liquid, is then added to the barrel of the syringe 100 in a sufficient quantity to make a 20-30% hyaluronic acid liquid formulation, as shown in FIG. 13C. The plunger 99 is then inserted into the syringe 100 and depressed such that the phosphate buffered saline 103 is pushed through the hyaluronic acid 102 creating a heterogenous hyaluronic acid liquid formulation 104, as shown in FIG. 13D. After 24 hours, the solution has a large number of trapped air bubbles 105, as shown in FIG. 13E, but the intervening areas are a homogenous 20-30% hyaluronic acid liquid formulation 106 that is transparent.

Figure 14A:
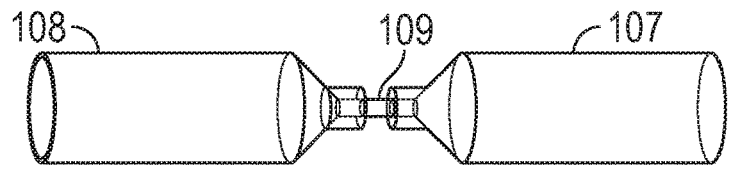
FIGS. 14A-E show an alternative method of compounding a liquid formulation of 20% hyaluronic acid.
Figure 14B:
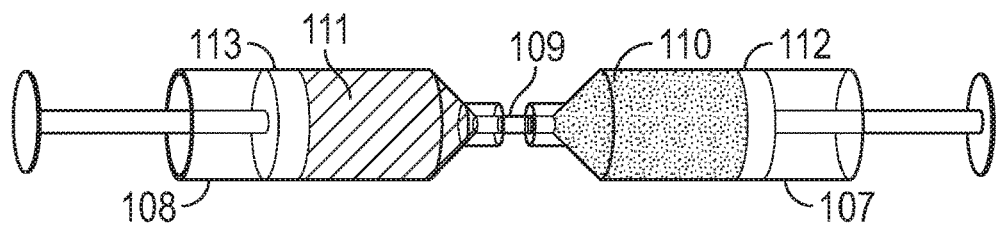
Figure 14C:
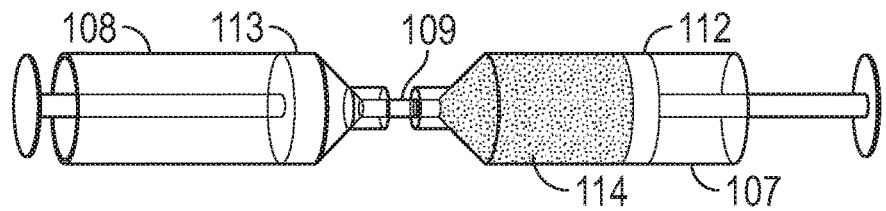
Figure 14D:
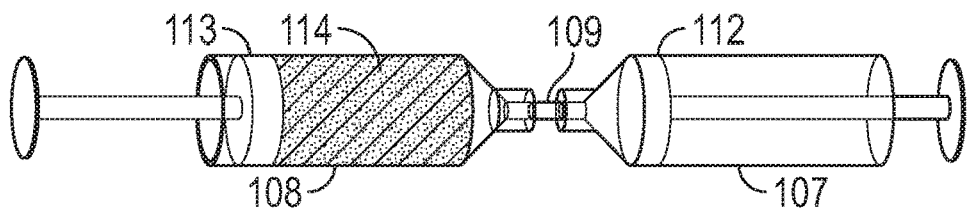
Figure 14E:
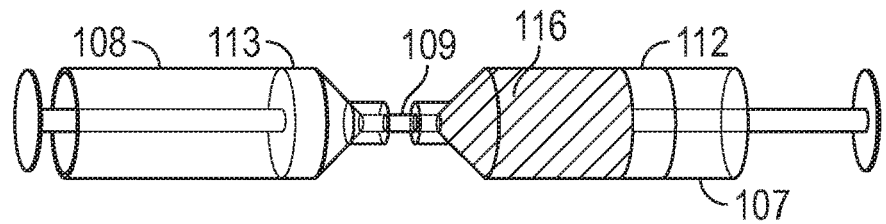

FIGS. 14A-E show an alternative method of compounding a liquid formulation of 20% Hyaluronic Acid. In this alternative method, the plungers from two syringes are removed, and the syringes 107 and 108 are coupled to each other using a syringe coupler 109, as shown in FIG. 14A. The barrel of one syringe 107 is filled with hyaluronic acid 110 followed by the plunger 112, as shown in FIG. 14B. The barrel of the other syringe 108 is filled with phosphate buffered saline followed by the other plunger 113. The plunger 113 of syringe 108 is depressed, and phosphate buffered saline 111 is pushed through the syringe coupler 109 into the other syringe 107, creating a heterogenous hyaluronic acid liquid formulation 114, as shown in FIG. 14C. The plunger 112 of syringe 107 is then depressed pushing the heterogenous hyaluronic acid solution 114 through the syringe coupler 109 and into the other syringe 108, as shown in FIG. 14D. This process is continued until a homogenous hyaluronic acid liquid formulation 116 is achieved, as shown in FIG. 14E, which requires between 5 and 25 exchanges between the two syringes. Once a homogeneous hyaluronic acid liquid formulation 116 is achieved, the empty syringe 108 and syringe coupler 109 can be removed.

EXAMPLE

Creation of 20% Hyaluronic Acid Solution

The plunger from a 10 mL luer lock syringe was removed and the syringe capped. The barrel of the syringe was filled with 1.0 gram of pharmaceutical grade hyaluronic acid 700 kDa, bioburden<10 cfu/g, endotoxin<0.01 EU/mg (Lifecore Biomedical LLC, Chaska, Minn.). The barrel of the syringe was then slowly filled with 4.5 mL phosphate buffered saline, pH 7.4 (Thermo Fisher Scientific, Waltham, Mass.) and 500 µL of 100× combination streptomycin, penicillin, amphotericin B (Thermo Fisher Scientific, Waltham, Mass.). The plunger was then reinserted into the barrel of the syringe. The syringe plunger was depressed to approximately halfway down the syringe barrel, pushing the phosphate buffered saline through the hyaluronic acid powder to the capped end of the syringe. Initially the solution was heterogenous and lacked transparency. The syringe was placed at 4° C. overnight. After 24 hours, the solution contained many small fixed bubbles, but the intervening areas were clear and homogenous.

An alternative method of hyaluronic acid mixing was also developed though not used for this ex vivo testing. A 10 mL luer lock syringe containing 1.0 gram of the above hyaluronic acid powder was coupled to a second 10 mL luer lock syringe containing 5 mL phosphate buffered saline, pH 7.4. The saline was first passed into the syringe containing the hyaluronic acid powder. The hyaluronic acid powder and saline were then passed back into the original syringe. This process of passing the solution between the two syringes was repeated approximately ten times yielding a homogenous solution.

Intraocular Injections

Fifty freshly enucleated porcine eyes (Animal Technologies Inc., Tyler, Tex.) were used for this study. Periocular tissues were removed from each eye and the optic nerve trimmed to 5 mm. The eyes were separated into six groups of ten eyes each. Group 1 was a control group that received no injection. Group 2 received a 0.1 µL injection of the above 20% hyaluronic acid solution. Group 3 received a 0.2 µL injection of the above 20% hyaluronic acid solution. Group 4 received a 0.3 µL injection of the above 20% hyaluronic acid solution. Group 6 received a 0.5 µL injection of the above 20% hyaluronic acid solution. For each injection, the solution was loaded into a 1 mL luer lock syringe and injected through the optic nerve into the vitreous cavity using a microneedle. Due to the viscosity of the solutions, it was not possible to inject these solutions through standard microneedles, and so a specially designed ½ inch 23-gauge needle with an internal diameter of 540 um was used for all injections. The internal diameter of this needle is larger than is commercially available with 23-gauge needles.

Qualitative Assessment

At 48 hours, the vitreous of all ten eyes in each group were removed. A qualitative assessment of the treated vitreous was made by comparing it to the control porcine vitreous and Provisc® viscoelastic preparation (Alcon, Fort Worth, Tex.).

Index of Refraction

Index of refraction was used to assess the changes in hyaluronic acid concentration in the vitreous cavity after intravitreal injection. One eye from each group was selected at random and 0.1 μL of vitreous was sampled at 24 hours and 48 hours after intravitreal injection. The mean refractive index of each sample was obtained from five readings measured with a digital refractometer (Model # Hi96800, Hanna Instruments, Woonsocket, R.I.).

Viscosity

The vitreous samples from each group were pooled. The viscosity of each of the resultant 5 pooled samples were tested using a Brookfield DV-II+ Pro Viscometer (Brookfield Engineering Laboratories, Inc., Middleboro, Mass.). Due to the expected non-Newtonian nature of the vitreous gel, viscosity measurements were made over a range of sheer rates (rpm). For measuring diffusion, 0.1 μL of artificial dye was added to the top of a container containing 5 mL of samples from Group 1 (vitreous), Group 2 (addition of 0.1 μL 20% HA), and Group 4 (addition of 0.3 μL 20% HA).

Results

Qualitative Assessment

Unlike the normal porcine vitreous, the vitreous after intravitreal injection of hyaluronic acid was significantly thicker and less mobile. Even with the smallest volume of 20% Hyaluronic Acid (group 2), the flow of vitreous was significantly reduced. There was a dose dependent effect on the vitreous, whereby increasing volumes of 20% hyaluronic acid resulted in less mobile vitreous, often with retention of bubbles within the gel. When compared to Provisc, group 2 and 3 were more mobile, while groups 3 and 4 were less mobile.

Changes in the Index of Refraction

Figure 15:
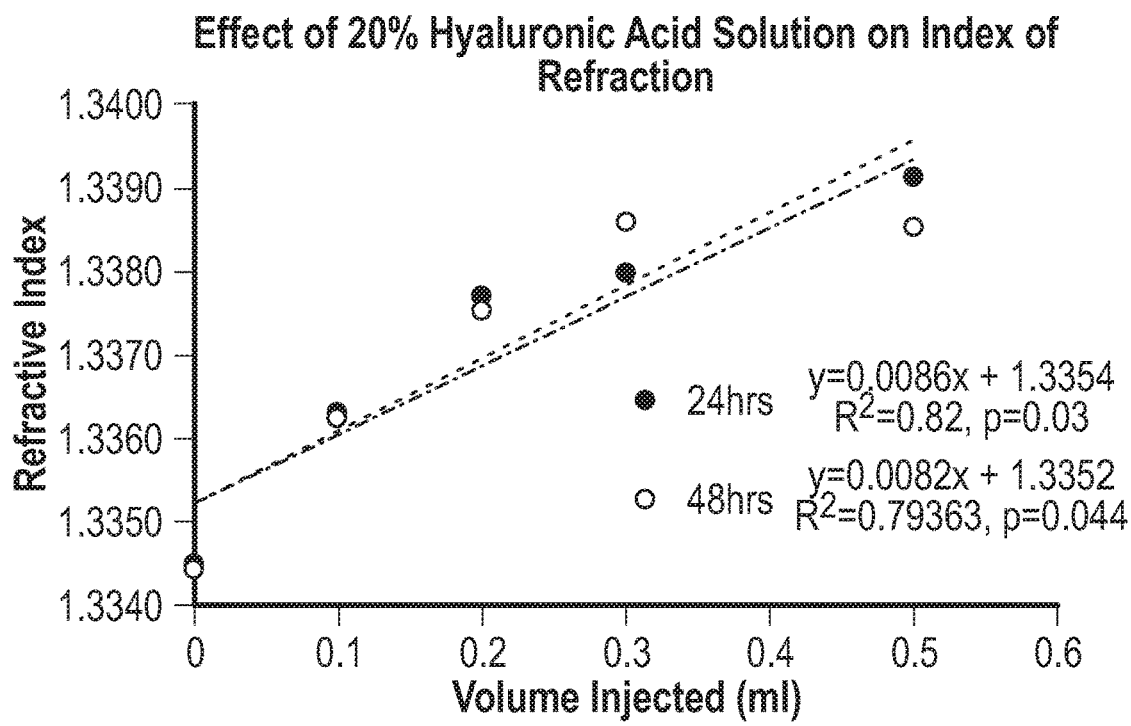
FIG. 15 illustrates the effect of intravitreal injection of a 20% hyaluronic acid solution on the index of refraction of the vitreous. Hyaluronic acid 700 kDa was compounded into a 20% solution with phosphate buffered saline and injected into the vitreous cavity of porcine eyes. With increasing volume of the highly concentrated hyaluronic acid, there is a corresponding increase in the index of refraction of the vitreous. A similar increase in the index of refraction in the vitreous occurs after 24 and 48 hours after intravitreal injection, indicating there is no significant degradation of intravitreal hyaluronic acid over this time frame.

As shown in FIG. 15, at 24 hours, the increase in index of refraction was directly related to the volume of the concentrated 20% hyaluronic acid injected into the vitreous cavity ($R2=0.82$, $p=0.03$). At 48 hours, there was a similar increase in index of refraction for a given volume of concentrated hyaluronic acid injected ($R2=0.79$, $p=0.044$). For each volume of hyaluronic acid injected, there was no significant difference between the 24- and 48-hour time point (Paired T-test, p-value=0.94), indicating there was no significant degradation of hyaluronic acid between the 24- and 48-hour time point.

Viscosity

Figure 16:
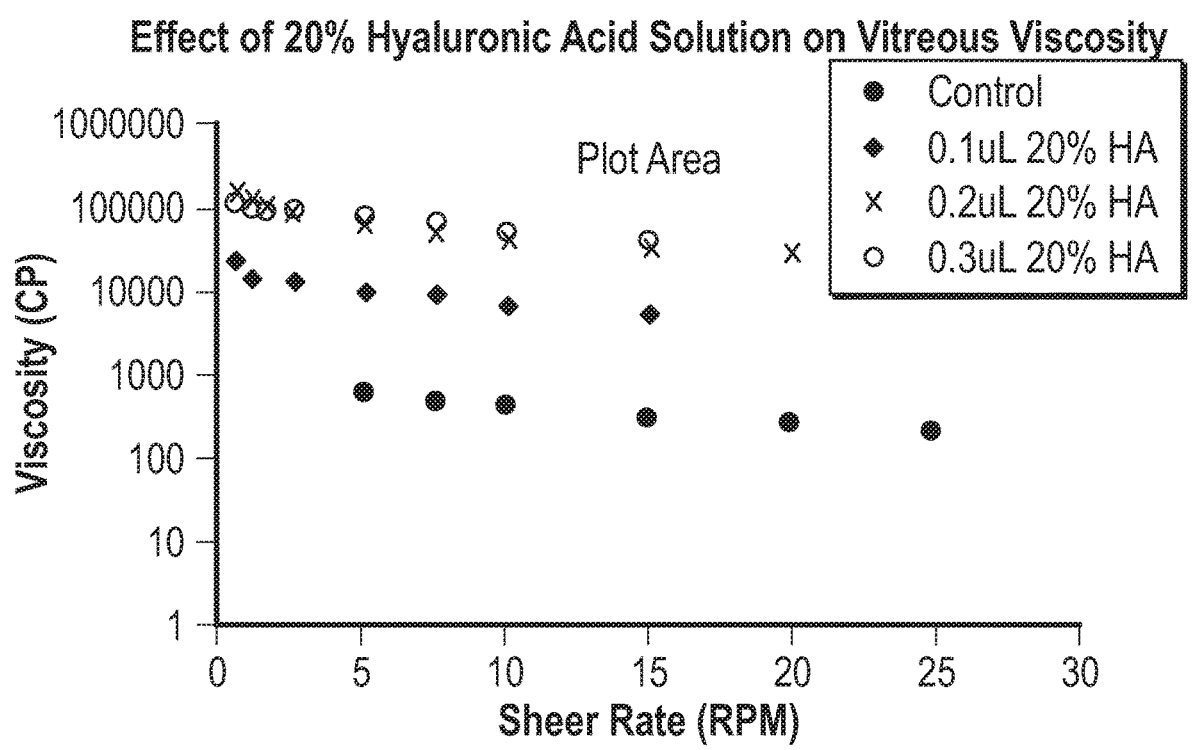
FIG. 16 illustrates the effect of 20% hyaluronic acid solution on vitreous viscosity. Hyaluronic acid 700 kDa was compounded into a 20% solution with phosphate buffered saline and injected into the vitreous cavity of porcine eyes. Forty-eight hours after injection, the vitreous was removed and the viscosity measured after different sheer rates. Unmodified porcine vitreous had a viscosity ranging from 123-600 cp, depending on the sheer rate. After 0.1 µL injection of 20% hyaluronic acid, the viscosity increased to 3325-21745 cp, a 15-30 fold increase. With both a 0.2 µL and 0.3 µL injection of 20% hyaluronic acid, the viscosity further increased to 37752-104000 cp, over 100 times greater than the original vitreous viscosity.

Due to the non-Newtonian behavior of the vitreous and hyaluronic acid solutions, measurements of viscosity were taken at a variety of different sheer values. Vitreous viscosity measurements ranged from 600 cp at 5 rpm to 123 cp at 80 rpm. Forty-eight hours after a 0.1 μL intravitreal injection of 20% hyaluronic acid, the viscosity of the vitreous increased 16 to 27 times, with viscosity measurements ranging from 9,613 cp to 3,325 cp at sheer rates of 5 rpm to 80 rpm, respectively. Viscosity was further increased by injections of either 0.2 μL or 0.3 μL of 20% hyaluronic acid. With both 0.2 μL and 0.3 μL, viscosity increased to over 110 times greater than the natural vitreous, with viscosity ranging from 70,585 cp at a sheer rate of 5 rpm to 37,752 cp at a sheer rate of 15 rpm, as shown in FIG. 16.

Discussion

Reducing the rate of flow of water through the vitreous by uniquely altering the physical characteristics of the vitreous offers a unique and novel, non-surgical intervention to treat rhegmatogenous retinal detachments. Successfully altering the vitreous to treat retinal detachments requires identification of a substance that can be injected in a small volume through a microneedle into the vitreous cavity, is biocompatible, and despite this small volume of injection, has a significant effect on the physical characteristics of the vitreous, namely increasing its viscosity and resistance to diffusion of water. Hyaluronic acid is a glycosaminoglycan that was originally isolated from the vitreous and is composed of long, negatively charged polymers that bind and restrict water. Furthermore, hyaluronic acid has over 40 years of use in the eye, skin, and knee and shows no adverse short or long-term effects. This study demonstrates that hyaluronic acid can be compounded into ultrahigh concentrated solutions of 20% or more hyaluronic acid. Due to these high concentrations, only small injection volumes are needed to dramatically alter the physical characteristics of the vitreous. With only a 0.2 μL injection of a 20% hyaluronic acid solution, the viscosity of the vitreous is increased over 110-fold. Such alteration in physical characteristics of the vitreous will significantly reduce flow of water from the ciliary body to the subretinal space, thereby allowing the retinal pigment epithelium to remove subretinal fluid faster than it accumulates, with a net result of retinal reattachment.

While the present invention envisions substances that slow the flow of water and/or solutes through a biologic tissue, any substance that can be formulated into a dry mass can be used with the present invention. The dry formulation of the substance can be compacted with or without a biodegradable coating. The dry formulation of the substance can be coated to facilitate passage through a small gauge needle. The substance can be any thickening agent that increases viscosity or slows down water and/or solute transport such as, but not limited to, natural gums, starches, pectins, agar-agar, gelatin, mechanical and thixotropic agents, and fumed silica. The substance can be any rheology modifier such as, but not limited to, polyurethanes, acrylic polymers, latex, styrene/butadiene, polyvinyl alcohol (PVA), cellulosics (cellulose acetate), cellulose triacetate, cellulose propionate, cellulose acetate propionate (CAP), cellulose acetate butyrate (CAB), nitrocellulose, cellulose sulfate, methyl cellulose, ethylcellulose, ethyl methyl cellulose, hydroxypropyl cellulose (HPC), hydroxyethyl methyl cellulose, ethyl hydroxyethyl cellulose, carboxymethyl cellulose (CMC), hydroxyl methylcellulose (HMC), hydroxylethyl cellulose, hydroxypropyl methylcellulose (HPMC), chemically modified cellulose macromolecules), sulfonates, gums (guar, anthan, cellulose, locust bean, acacia), saccarides (carrageenan, pullulan, konjac, alginate), proteins (casein, collagen, albumin), modified castor oil, organosilicones (silicone resins, dimethicones, modified silicones), synthetic hydrogels (polyvinyl alcohol, sodium polyacrylate, acrylate polymers and copolymers), organogels, xerogels, natural hydrogels (agrose, methylcellulose, hyaluronan, chondroitin sulfate), modified hydrogels, cross-linked hydrogels, polyionic polymers, and nanocomposite hydrogels.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of reattaching a detached retina of an eye, the method comprising:
   injecting a substance comprising hyaluronic acid formulated as a solution with a concentration greater than 5% by weight into a vitreous cavity of the eye; and
   slowing flow of water and/or solutes through fluid in the vitreous cavity into a subretinal space by the substance to reduce a rate of accumulation of a subretinal fluid in the subretinal space to below a rate of removal of the subretinal fluid from the subretinal space by retinal pigment epithelium to reattach the retina.

2. The method of claim 1, wherein the substance slows flow of the fluid through a tear in the retina into the subretinal space.

3. The method of claim 1 further comprising increasing a viscosity of the fluid in the vitreous cavity.

4. The method of claim 1 wherein the fluid is vitreous fluid.

5. The method of claim 1, wherein the substance comprises hyaluronic acid formulated as a solution with a concentration greater than 15% by weight.

6. The method of claim 1, wherein the substance comprises hyaluronic acid formulated as a solution with a concentration greater than 30% by weight.

7. The method of claim 1, wherein the substance further comprises a therapeutic agent.

8. The method of claim 7, wherein the therapeutic agent comprises a neuroprotective agent.

9. The method of claim 7 wherein the therapeutic agent comprises an agent that inhibits photoreceptor cell death.

10. The method of claim 1, wherein injecting a substance comprises injecting a substance with a volume between 0.05 mL to 0.5 mL.

11. The method of claim 10 further comprising removing fluid from the eye prior to the injecting step.

12. The method of claim 10, wherein the injecting step is performed without removing fluid from the eye prior to the injecting step.

13. The method of claim 1, wherein the injecting step comprises:
   inserting a needle into the vitreous cavity; and
   delivering the substance from a reservoir through the needle into the vitreous cavity.

14. The method of claim 13, wherein the delivering step comprises moving a plunger within the reservoir.

15. The method of claim 1, wherein the substance comprises a modified form of hyaluronic acid.

16. The method of claim 1, wherein the substance comprises a hydrogel.

17. The method of claim 1, wherein the substance comprises a natural hydrogel.

18. The method of claim 1, wherein the substance comprises a synthetic hydrogel.

19. The method of claim 1, wherein the substance comprises a modified hydrogel.

20. The method of claim 1, wherein the substance comprises a cross-linked hydrogel.

21. The method of claim 1, wherein the fluid comprises saline.

22. A method of reattaching a detached retina of an eye, the method comprising:
   injecting a substance comprising hydroxypropyl methylcellulose (HPMC) formulated as a solution with a concentration greater than 5% by weight into a vitreous cavity of the eye; and
   slowing flow of water and/or solutes through fluid in the vitreous cavity into a subretinal space by the substance to reduce a rate of accumulation of a subretinal fluid in the subretinal space to below a rate of removal of the subretinal fluid from the subretinal space by retinal pigment epithelium to reattach the retina.

23. The method of claim 22, wherein the substance comprises hydroxypropyl methylcellulose (HPMC) formulated as a solution with a concentration greater than 15% by weight.

24. The method of claim 22, wherein the substance comprises hydroxypropyl methylcellulose (HPMC) formulated as a solution with a concentration greater than 30% by weight.

25. The method of claim 22, wherein injecting a substance comprises injecting a substance with a volume between 0.05 mL to 0.5 mL.

26. The method of claim 25 further comprising removing fluid from the eye prior to the injecting step.

27. The method of claim 25, wherein the injecting step is performed without removing fluid from the eye prior to the injecting step.

28. A method of reattaching a detached retina of an eye, the method comprising:
   injecting a substance having a viscosity of greater than 10,000,000 (cps) (resting) and 500,000 (cps) (dynamic) into a vitreous cavity of the eye; and
   slowing flow of water and/or solutes through fluid in the vitreous cavity into a subretinal space by the substance to reduce a rate of accumulation of a subretinal fluid in the subretinal space to below a rate of removal of the subretinal fluid from the subretinal space by retinal pigment epithelium to reattach the retina.

29. The method of claim 28, wherein injecting a substance comprises injecting a substance with a volume between 0.05 mL to 0.5 mL.

30. The method of claim 29 further comprising removing fluid from the eye prior to the injecting step.

31. The method of claim 29, wherein the injecting step is performed without removing fluid from the eye prior to the injecting step.

* * * * *